United States Patent
Rajek

(10) Patent No.: US 9,504,489 B2
(45) Date of Patent: Nov. 29, 2016

(54) CANNULATED MEDICAL INSTRUMENT HANDLE WITH AN AIRSPACE

(71) Applicant: Andrew Rajek, Kenosha, WI (US)

(72) Inventor: Andrew Rajek, Kenosha, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 434 days.

(21) Appl. No.: 14/016,950

(22) Filed: Sep. 3, 2013

(65) Prior Publication Data

US 2014/0371755 A1 Dec. 18, 2014

Related U.S. Application Data

(60) Provisional application No. 61/834,338, filed on Jun. 12, 2013.

(51) Int. Cl.
*A61B 17/88* (2006.01)
*A61B 17/34* (2006.01)
*A61B 17/00* (2006.01)

(52) U.S. Cl.
CPC .... *A61B 17/3421* (2013.01); *A61B 2017/0046* (2013.01); *A61B 2017/00407* (2013.01)

(58) Field of Classification Search
CPC .......... A61B 17/8861; A61B 17/3421; A61B 2017/00407; A61B 2017/0046; A61C 1/001; A61C 1/10; A61C 1/12; A61C 3/00; B25G 1/105; B25B 23/12
USPC ........ 606/279, 86 A, 103, 104, 79–85, 86 R, 606/96–99; 433/103–104, 114–116; 81/177.1, 489, 900
See application file for complete search history.

(56) References Cited

U.S. PATENT DOCUMENTS

| | | | |
|---|---|---|---|
| 5,320,626 A | 6/1994 | Schmieding | |
| 5,501,688 A * | 3/1996 | Whiteside | A61B 17/8861 140/119 |
| 5,573,529 A * | 11/1996 | Haak | A61B 19/44 128/898 |
| 8,216,243 B2 * | 7/2012 | Yevmenenko | A61B 17/863 606/104 |
| 8,298,247 B2 | 10/2012 | Albertorio et al. | |
| 8,333,774 B2 | 12/2012 | Morrison | |
| 8,366,559 B2 | 2/2013 | Papenfuss et al. | |
| 2003/0091953 A1* | 5/2003 | Cheney | A61C 1/088 433/29 |
| 2005/0033365 A1 | 2/2005 | Courage | |
| 2006/0116680 A1* | 6/2006 | Kugler | A61B 17/92 606/86 B |
| 2009/0082818 A1* | 3/2009 | Roth | A61B 17/562 606/304 |
| 2010/0298838 A1* | 11/2010 | Walters | E04G 1/24 606/104 |

* cited by examiner

*Primary Examiner* — Mary Hoffman
*Assistant Examiner* — Tara R Carter
(74) *Attorney, Agent, or Firm* — Absolute Technology Law Group, LLC

(57) ABSTRACT

A cannulated medical instrument handle apparatus comprises a handle housing component with a hollow handle insert channel and a tubular insert that fits within the handle insert channel. The airspace chamber created between the inner walls of said channel and the outer walls of said insert provides the handle with increased susceptibility to sterilization of the cannula lumen.

22 Claims, 5 Drawing Sheets

CANNULATED MEDICAL INSTRUMENT HANDLE WITH AN AIRSPACE

CROSS-REFERENCE TO RELATED APPLICATIONS

This application claims priority to U.S. Provisional Application No. 61/834,338 filed on Jun. 12, 2013.

FIELD OF INVENTION

This invention relates to the field of medical devices, and more specifically to a cannulated medical instrument handle structurally adapted for high temperature sterilization of inner core elements.

TERMS OF ART

Figure 1:
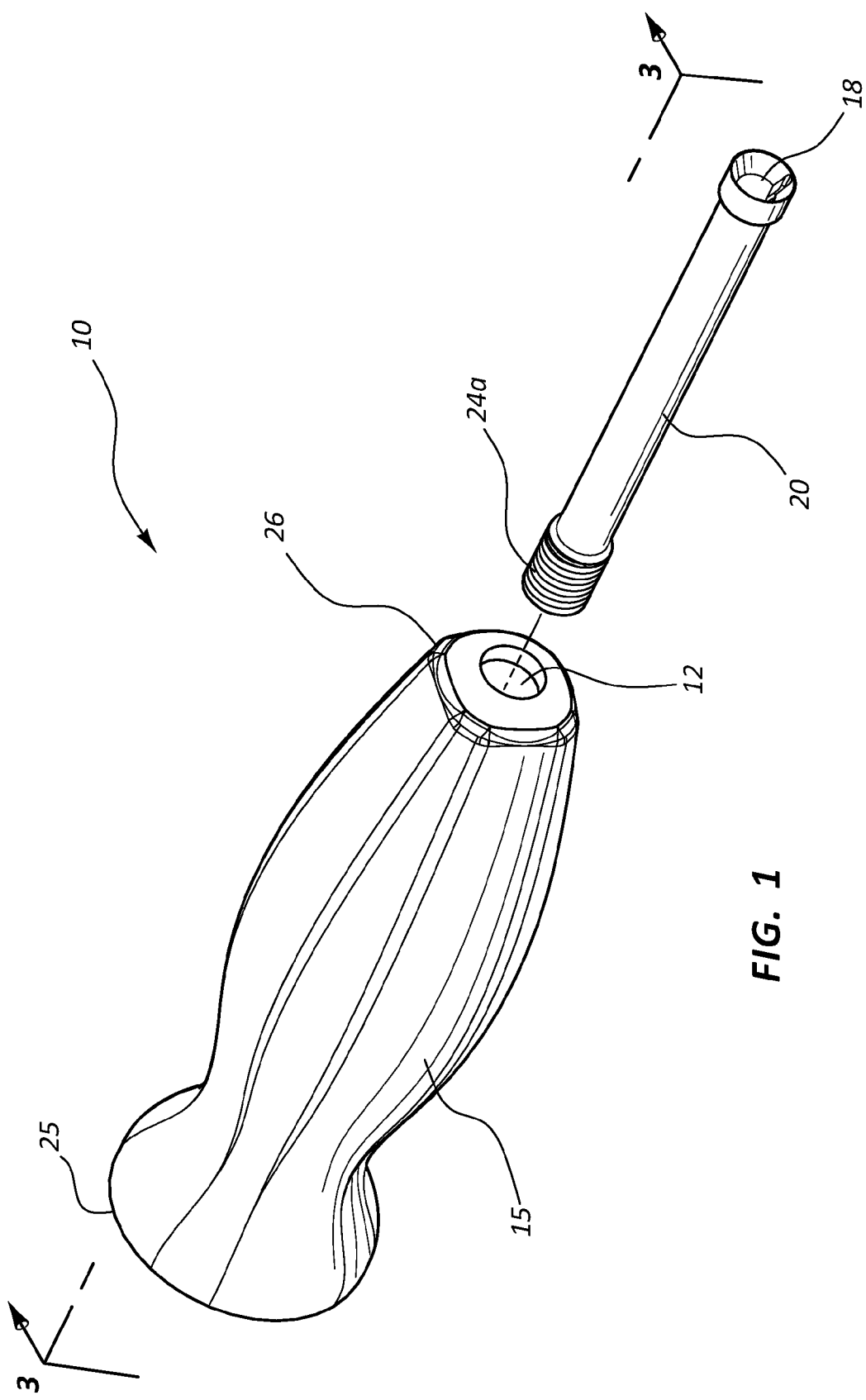
FIG. 1 illustrates an exploded isometric view of a cannulated medical instrument handle.

As used herein, the term "airspace chamber" means the hollow middle section of the handle insert channel with internal diameter $D_3$ which acts a thermal barrier permitting tubular insert to obtain and retain ambient temperature.

As used herein, the term "conformed" means structurally configured to conform to geometric dimensions and characteristics.

As used herein, the term "convex end" means a rounded end component.

As used herein, the term "distal" means the location situated further from the user.

As used herein, the term "external diameter $D_1$" means the measurement taken from the top exterior surface of the housing component to the bottom exterior surface of the housing component, taken at any point along the housing.

As used herein, the term "external diameter $D_{tubext}$" means the measurement taken from the top exterior surface of the tubular insert to the bottom exterior surface of the tubular insert, taken at any point along the insert within the tubular shaft segment.

As used herein, the term "internal diameter $D_2$" means the measurement taken from the top interior surface of the housing component to the bottom interior surface of the housing component, taken at any point along the housing within the distal threaded segment.

As used herein, the term "internal diameter $D_3$" means the measurement taken from the top interior surface of the housing component to the bottom interior surface of the housing component, taken at any point along the housing within the proximal smooth bore segment.

As used herein, the term "internal diameter $D_{tubint}$" means the measurement taken from the top interior surface of the tubular insert to the bottom interior surface of the tubular insert, taken at any point along the insert within the tubular shaft segment.

As used herein, the term "length $L_3$" means the length of the interior airspace chamber, which is the measurement taken from the distal edge of the proximal smooth bore segment to the proximal edge of the proximal smooth bore segment.

As used herein, the term "lumen" means a cannula or hollow shaft that runs through the center of the tubular insert, from the anterior insert aperture to the posterior insert aperture.

As used herein, the term "proximal" means the location situated nearer to the user.

As used herein, the term "volume $V_{air}$" means the volume of the interior airspace chamber, which is a function of interior diameter $D_3$, the external diameter $D_{tubext}$, and length $L_3$, which is the length of the interior airspace chamber.

As used herein, the term "wall thickness $W_3$" means the measurement taken from the top exterior surface of the housing component to the top interior surface of the housing component, taken at any point along the housing within the proximal smooth bore segment.

As used herein, the term "wall thickness $W_{tub}$" means the measurement taken from the top exterior surface of the tubular insert to the top interior surface of the tubular insert, taken at any point along the insert within the tubular shaft segment.

BACKGROUND

Among hospital patients that have surgery, it is estimated that approximately 2 percent develop a surgical site infection (SSI), and among those who develop an SSI, it is estimated that approximately 3 percent die as a result. It is a problem known in the art that unclean medical instruments are one direct cause of SSIs. Despite scrupulous adherence to cleaning and sterilization standards, which include a multi-step process of rinsing, scrubbing and sterilization, instruments may fail to become sufficiently clean or sterile.

Cleaning and sterilization of cannulated instruments is particularly challenging. A cannulated medical instrument contains a hollow shaft, known as a lumen, running straight through the center of the instrument, through which a surgeon may introduce, position, manipulate and/or remove surgical and biological material directly to or from the surgical site inside the patient's body. Operating through the center of a medical instrument allows a surgeon to operate with great precision and through a smaller incision, creating the potential for reduced trauma and a better surgical outcome. However, it is a problem known in the art that the interior of a narrow lumen can be difficult to clean and sterilize.

Every surface of a medical instrument must be cleaned and sterilized between uses, including lumen's interior surface. Rinsing and scrubbing steps in the cleaning process should remove physical debris, but then the entire interior surface of the lumen must reach sterilization temperature in an autoclave in order to effectively kill pathogens and meet sterilization requirements. Changing standards in how instruments are sterilized in an autoclave (e.g., reduced cycle time in the autoclave; increased use of autoclave bins with few access holes to allow superheated steam to directly contact instruments) have made sterilization more difficult to achieve than ever before, and some prior art handles may no longer be able to meet sterilization requirements.

Autoclave tests of prior art cannulated medical instruments have demonstrated that instruments with narrow interior diameters in the lumen take longer to reach sterilization temperature in the middle of the lumen as compared to instruments with wider interior diameters in the lumen. This may be attributed to the greater volume of the structure surrounding a narrower lumen. An instrument with the same overall exterior dimensions but with a wider lumen has thinner walls around the lumen and thus has less mass to absorb heat and impede the rise in temperature as the instrument is heated to sterilization temperature.

It is desirable to have a medical instrument which offers the surgical benefits of a cannulated instrument but which is capable of being sterilized and cleaned in a manner that meets sterilization requirements and thus prevents SSIs.

It is desirable to have a cannulated medical instrument with a wider lumen or internal chamber to increase the effectiveness of sterilization in an autoclave.

It is further desirable to have a cannulated medical instrument with less mass surrounding the lumen or internal chamber to further increase the effectiveness of sterilization in an autoclave.

SUMMARY OF THE INVENTION

The present invention is a cannulated medical instrument handle apparatus comprised of a handle housing component that is partially enclosed within a conformed outer silicone layer. A tubular insert within the handle housing component creates an airspace chamber between the exterior of the tubular insert and an interior housing channel of the handle housing component.

The handle housing component has an inner surface and an outer surface, as well as a substantially closed proximal convex end, a distal receiving end, and the interior housing channel that creates the interior airspace chamber. The distal receiving end of the handle housing component has a housing aperture which is adapted to receive a ratcheting mechanism. The interior housing channel is threaded at a distal end.

The tubular insert has an distal end, a tubular shaft segment having a lumen running through its center, and a proximal end. The distal end is externally threaded to interface with the internally threaded portion of the interior housing channel.

The tubular insert has a constant external diameter $D_{tubext}$ and an internal diameter $D_{tubint}$. The interior housing channel has an internal diameter $D_3$ and a length $L_1$.

The volume $V_{air}$ of the airspace chamber is proportional to the difference between the tubular insert diameter $D_{tubext}$ and the internal housing channel diameter $D_3$, as well as the length $L_3$ of the interior airspace chamber. Internal airspace chamber dimensions $D_3$ and $L_3$ are designed to enlarge volume $V_{air}$ of the airspace chamber so that the handle housing component can efficiently reach a target sterilization temperature within an autoclave.

DETAILED DESCRIPTION OF INVENTION

For the purpose of promoting an understanding of the present invention, references are made in the text to exemplary embodiments of a cannulated medical instrument handle, only some of which are described herein. It should be understood that no limitations on the scope of the invention are intended by describing these exemplary embodiments. One of ordinary skill in the art will readily appreciate that alternate but functionally equivalent components and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale. Instead, emphasis has been placed upon illustrating the principles of the invention. Like reference numerals in the various drawings refer to identical or nearly identical structural elements.

Moreover, the terms "substantially" or "approximately" as used herein may be applied to modify any quantitative representation that could permissibly vary without resulting in a change in the basic function to which it is related.

FIG. 1 illustrates an exploded isometric view of a cannulated medical instrument handle 10 as it appears before assembly. Handle 10 has a distal receiving end 25 and a proximal convex end 26. A tubular insert 20 is inserted via a housing aperture 12 at proximal convex surface 26.

Handle 10 has an outer silicone layer 15. Said silicone layer substantially covers the exterior of said handle. Said outer silicone layer also forms part of housing aperture 12 at proximal convex surface 26.

In the embodiment shown, tubular insert 20 is a single machined piece that has a distal end with distal external threads 24a and a proximal segment 18.

Figure 2:
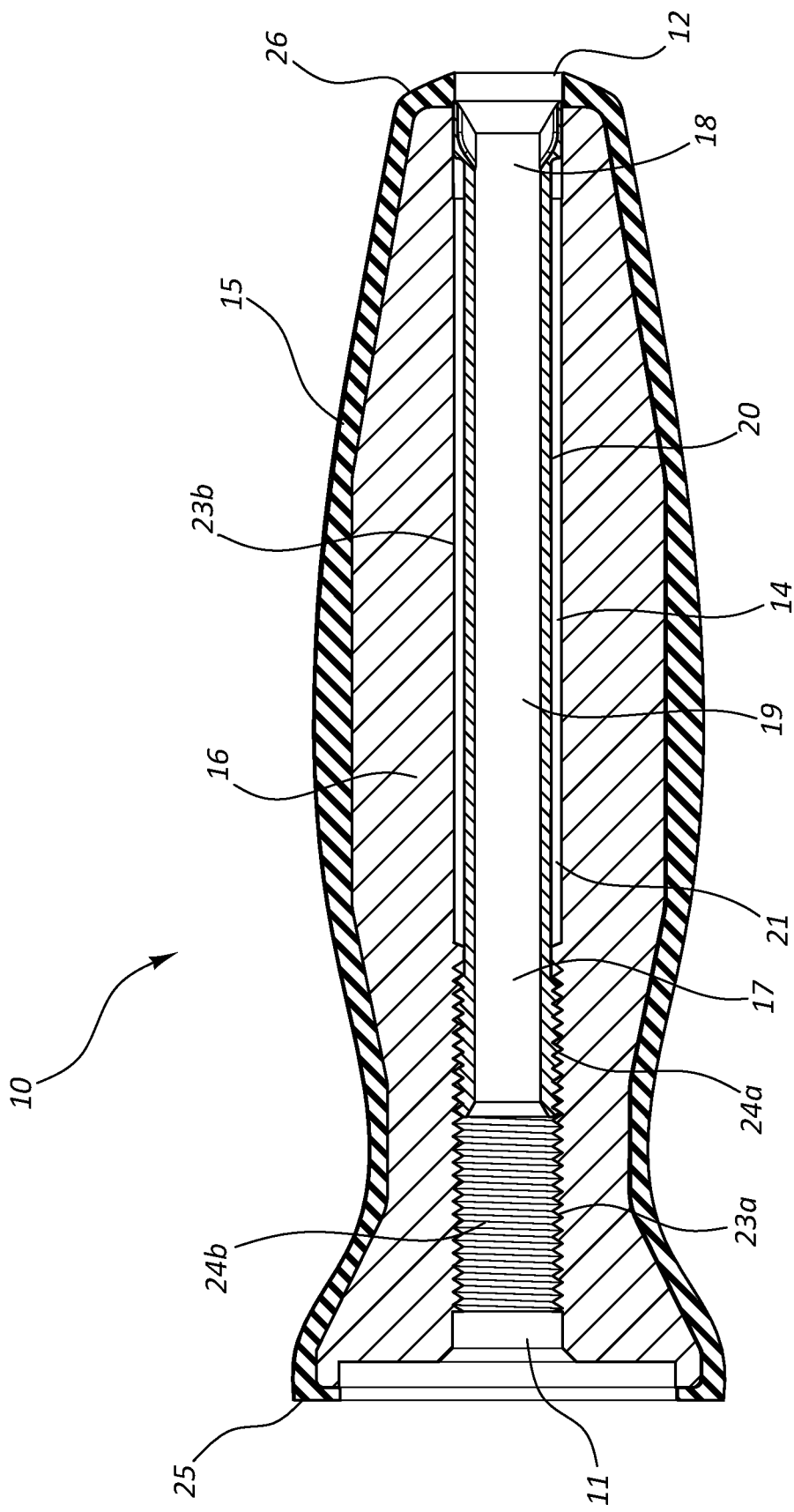
FIG. 2 illustrates a cross-section view of a cannulated medical instrument handle in assembled state.

FIG. 2 illustrates a cross-section view of a cannulated medical instrument handle 10 as it appears fully assembled. In the embodiment shown, tubular insert 20 is a single machined piece that has a distal end 17 with external threads 24a and a tubular shaft segment 19. Said tubular shaft segment 19 has a length equal to that of $L_3$ and ranging from about 0.500 inches to about 5.500 inches. Said tubular insert 20 is comprised of a heat conducting metal such as a surgical-grade stainless steel, alloys or other metals Said tubular insert 20 further has an internal diameter $D_{tubint}$ ranging from about 0.100 inches to about 0.180 inches, an external diameter $D_{tubext}$ ranging from about 0.137 inches to about 0.254 inches, and a wall thickness $W_{tub}$ ranging from about 0.037 inches to about 0.074 inches. Said internal diameter enables the interior lumen of the tubular shaft segment 19 to accommodate the passage of medical devices, such as k-wires. Said wall thickness enables the interior lumen of the tubular shaft segment 19 to efficiently reach sterilization temperature in an autoclave when cannulated medical instrument handle 10 is being cleaned.

Handle 10 has an inner housing component 16 which is comprised of heat conducting metal such as aluminum, stainless steel, alloys or other metals. Said inner housing component 16 includes handle insert channel 14, which has several distinct sections or segments: a first segment comprising a distal segment 23a that terminates at distal receiving end 25 and a second segment comprising a smooth bore segment 23b that terminates at proximal convex surface 26. Distal segment 23a has internal threads 24b. When tubular insert 20 is inserted into smooth bore 23a, the two components form an airspace chamber 21.

As illustrated in FIG. 2, said housing component 16 has an external diameter $D_1$, a first internal diameter $D_2$ at the distal segment 23a, and a second internal diameter $D_3$ at the smooth bore 23b. These values of $D_1$ and $D_3$ may be constant or may vary along the length of the respective exterior segment and smooth bore segment.

Said handle housing component 16 also has a wall thickness $W_3$ determined by $D_1$-$D_3$. An appropriate wall thickness enables the interior lumen of the tubular shaft segment 19 to efficiently reach sterilization temperature in an autoclave when cannulated medical instrument handle 10 is being cleaned.

As further illustrated in the exemplary embodiment in FIG. 2, tubular insert 20 has a constant external diameter $D_{tubext}$ for the entire length of its tubular shaft segment 19, such that when tubular insert 20 is installed within handle insert channel 14 this provides an interior airspace chamber 21 within handle insert channel 14 that efficiently reaches sterilization temperature in an autoclave when cannulated medical instrument handle 10 is being cleaned. In various embodiments, environments and applications, the sterilization temperature may be 270 degrees Fahrenheit, plus or minus about 10 percent. In various embodiments this temperature is sustained from two to twenty minutes. The sterilization temperature is the measured temperature of the chamber in which the instrument is sterilized. Testing environments and processes may also measure temperature inside the cannula, and these measured temperatures will also be 270 degrees plus or minus about 10 percent.

The volume of $V_{air}$ of interior airspace chamber 21 is determined by subtracting the external diameter $D_{tubext}$ of the tubular insert 20 from the second internal diameter $D_3$ of inner housing component 16, and multiplying the resulting value by length $L_3$ of the smooth bore segment 23a. This resultant value of $V_{air}$ may range from about 0.113 in$^3$ to about 0.432 in$^3$.

FIG. 2 also illustrates the distal end of handle insert channel 14 which contains a receiver 11 having a section of threads 24b designed to receive interchangeable medical devices. These devices, such as a ratcheting mechanism, can thereby be attached to medical instrument handles.

Figure 3:
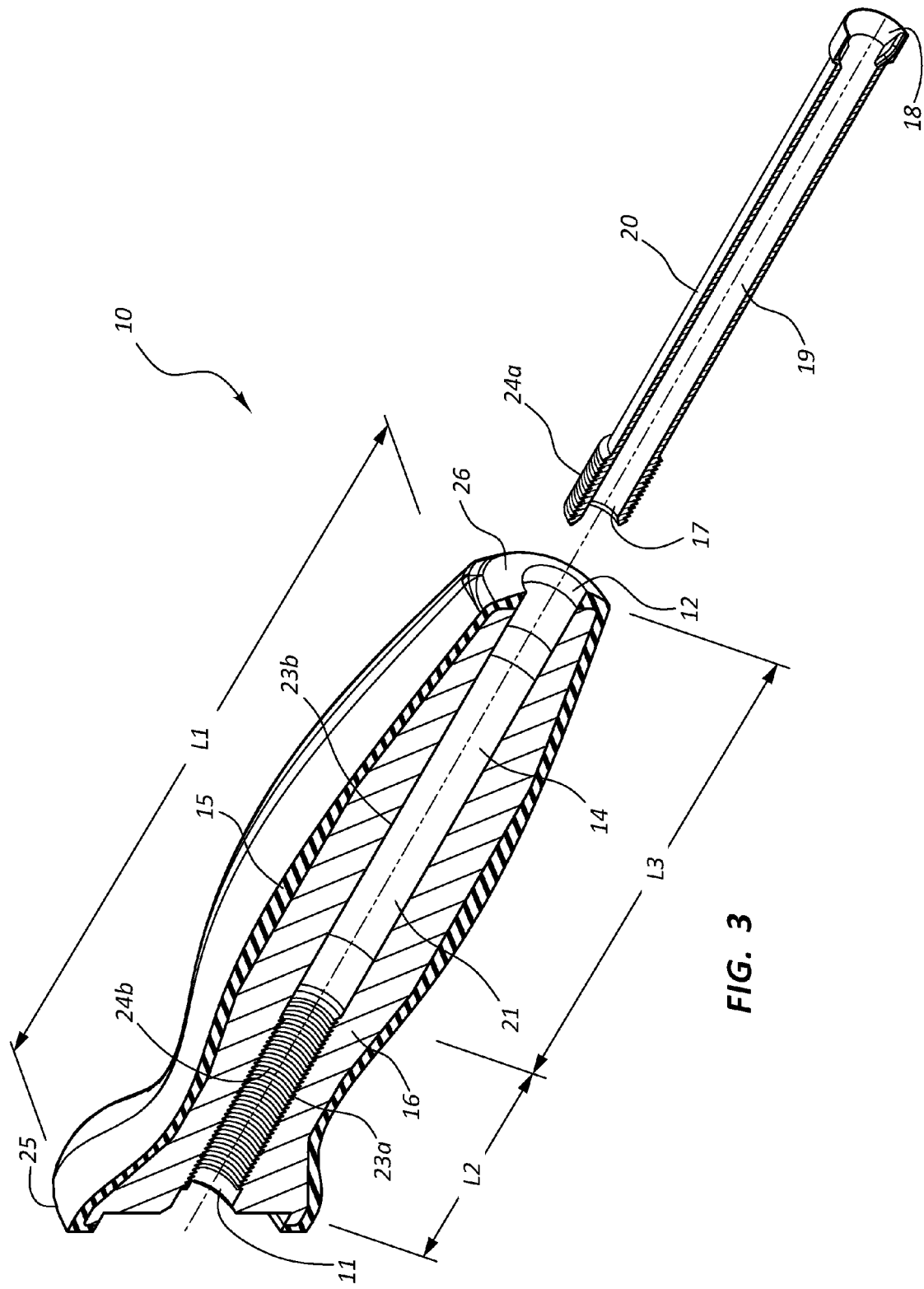
FIG. 3 illustrates an exploded isometric cross-section view of a cannulated medical instrument handle.

FIG. 3 illustrates an exploded isometric view of a cannulated medical instrument handle 10 as it appears before assembly. Tubular insert 20 is inserted into handle insert channel 14 through round housing aperture 12. As illustrated in the exemplary embodiment in FIG. 2, tubular insert 20 fits into inner housing 16 through round housing aperture 12. The external threads 24a of tubular insert 20 then interface with the internal threads 24b of distal segment 23b.

Figure 4:
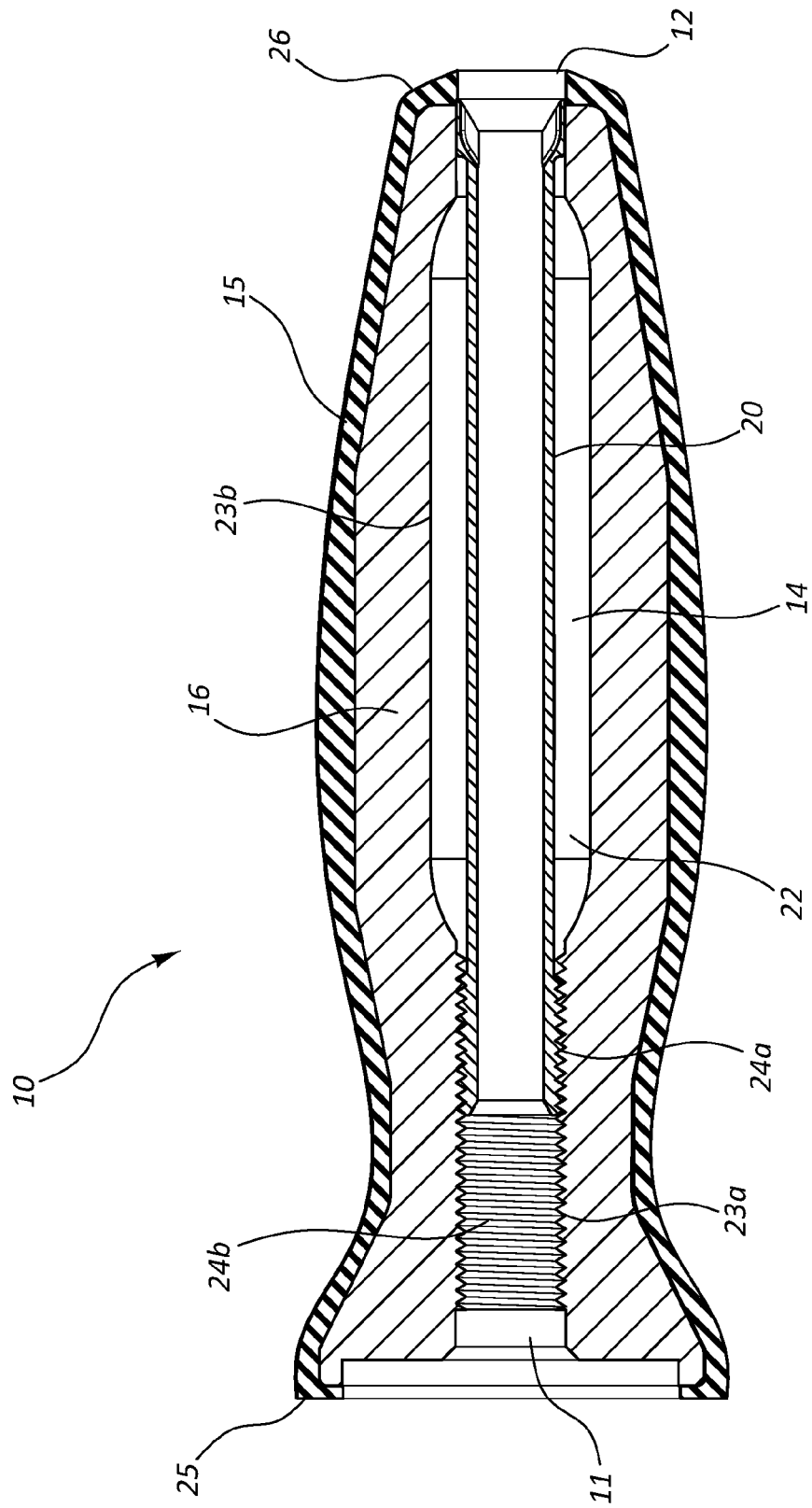
FIG. 4 illustrates a cross-section view of a second embodiment of a cannulated medical instrument handle in assembled state
Figure 5:
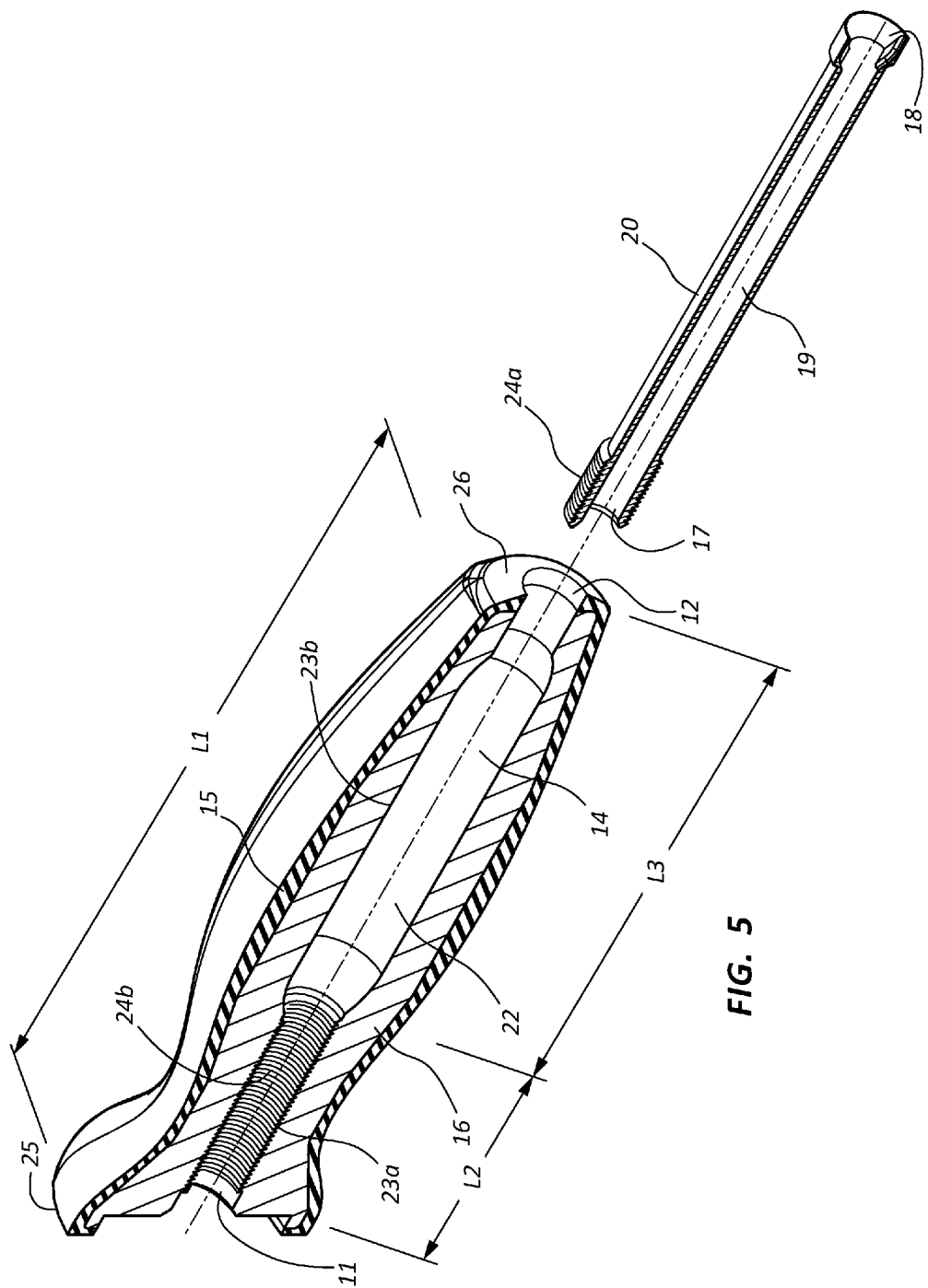
FIG. 5 illustrates an exploded isometric cross-section view of a second embodiment of a cannulated medical instrument handle.

FIGS. 4 and 5 illustrate an additional embodiment of a cannulated medical instrument handle 10. All part numbers found within the FIGS. 4 and 5 directly correspond to the part numbers from the previous embodiment of FIGS. 1-3, save for the airspace chamber, which is numbered 22.

FIG. 4 illustrates a cross-section view of an additional embodiment of a cannulated medical instrument handle 10 as it appears fully assembled. In the embodiment shown, airspace chamber 22 is of a significantly increased volume $V_{air}$, thereby enabling handle 10 to more efficiently reach a target sterilization temperature within an autoclave.

FIG. 5 illustrates an exploded isometric view of an additional embodiment of a cannulated medical instrument handle 10 as it appears before assembly. As shown in FIG. 4, airspace chamber 22 is of a significantly increased volume $V_{air}$, thereby enabling handle 10 to more efficiently reach a target sterilization temperature within an autoclave.

What is claimed is:

1. A handle apparatus for a medical instrument comprising:
   a housing component;
   wherein said housing component is made of a first thermally conductive material and includes an interior housing channel,
   wherein said interior housing channel has a threaded portion and a portion adapted to receive a tubular insert,
   wherein said tubular insert comprised of a second thermally conductive material;
   wherein said housing component includes
      a first housing diameter $D_1$ which corresponds to the external diameter of said housing component,
      a second housing diameter $D_2$ which corresponds to a first internal diameter of said housing component located within said threaded interior portion,
      a third housing diameter $D_3$ which corresponds to a second internal diameter of said housing component located within said portion adapted to receive a tubular insert,
      a first housing length $L_1$ which corresponds to the external length of said housing component,
      a first channel length $L_2$ which corresponds to a first interior channel length of said threaded interior portion, and
      a second channel length $L_3$ which corresponds to a second interior channel length of said portion adapted to receive a tubular insert;
   wherein a length of said tubular insert is less than said first housing length $L_1$;
   a tubular insert adapted for insertion into said housing channel, said tubular insert having an internal diameter $D_{tubint}$ and external diameter $D_{tubext}$ wherein $D_{tubext}$<$D_3$, said tubular insert having an interior lumen temperature T, wherein T is about 243 to 297 degrees Fahrenheit during sterilization;
   an airspace chamber located between said interior housing channel and said tubular insert wherein the radial dimension of said airspace chamber is defined by $D_3$-$D_{tubext}$.

2. The apparatus of claim 1 wherein the volume $V_{air}$ of said airspace chamber is calculated by the formula: $V_{air}$=$(D_3-D_{tubext})*L_3$.

3. The apparatus of claim 2 wherein said interior lumen temperature T is variably dependent on said airspace chamber volume $V_{air}$.

4. The apparatus of claim 2 wherein said airspace chamber volume $V_{air}$ ranges from about 0.113 in$^3$ to about 0.432 in$^3$.

5. The apparatus of claim 2, wherein the ratio of $V_{air}$:$L_3$ ranges from about 0.113:5.5 to about 0.432:0.5.

6. The apparatus of claim 1 wherein said second channel length $L_3$ ranges from about 0.500 inches to about 5.500 inches.

7. The apparatus of claim 1 wherein said tubular insert internal diameter $D_{tubint}$ ranges from about 0.100 inches to about 0.180 inches.

8. The apparatus of claim 1 wherein said tubular insert external diameter $D_{tubext}$ ranges from about 0.137 inches to about 0.254 inches.

9. The apparatus of claim 1 wherein said handle housing component has a first wall thickness $W_2$ determined by $D_1$-$D_2$ and second wall thickness $W_3$ determined by $D_1$-$D_3$.

10. The apparatus of claim 9 wherein said interior lumen temperature T is variably dependent on said second wall thickness $W_3$.

11. The apparatus of claim 1 wherein said tubular insert has a wall thickness $W_{tub}$ determined by $D_{tubext}$-$D_{tubint}$.

12. The apparatus of claim 11 wherein said tubular insert wall thickness $W_{tub}$ ranges from about 0.037 inches to about 0.074 inches.

13. The apparatus of claim 11 wherein said interior lumen temperature T is variably dependent on said tubular insert wall thickness $W_{tub}$.

14. The apparatus of claim 1 wherein said apparatus further includes a silicone outer layer which substantially covers said housing, and which is substantially conformed to the exterior contours of said housing.

15. The apparatus of claim 14 wherein said silicone covering has a proximal port or aperture for passing a surgical device.

16. The apparatus of claim 15 wherein said surgical device is a k-wire.

17. The apparatus of claim 1 wherein said handle apparatus is configured to permit the attachment of a mechanism at the distal end of said handle apparatus.

18. The apparatus of claim 17 wherein said mechanism is a ratcheting mechanism.

19. The apparatus of claim 1 wherein said airspace chamber dimension varies in proportion to said housing diameter $D_3$.

20. The apparatus in claim 1 wherein said airspace chamber dimension varies in proportion to said housing diameter $D_1$.

21. The apparatus of claim 1 wherein said housing diameter $D_1$ is variable along said first housing length $L_1$.

22. The apparatus of claim 1 wherein said housing diameter $D_1$ is not variable along said first housing length $L_1$.

* * * * *